United States Patent
Meadows

(10) Patent No.: US 10,857,350 B2
(45) Date of Patent: Dec. 8, 2020

(54) LEAD SPLITTER FOR NEUROSTIMULATION SYSTEMS

(71) Applicant: ImThera Medical, Inc., San Diego, CA (US)

(72) Inventor: Paul M. Meadows, Glendale, CA (US)

(73) Assignee: ImThera Medical, Inc., Houston, TX (US)

( * ) Notice: Subject to any disclaimer, the term of this patent is extended or adjusted under 35 U.S.C. 154(b) by 202 days.

(21) Appl. No.: 15/988,452

(22) Filed: May 24, 2018

(65) Prior Publication Data

US 2018/0264269 A1    Sep. 20, 2018

Related U.S. Application Data

(63) Continuation of application No. 14/771,625, filed as application No. PCT/US2014/019776 on Mar. 3, 2014, now Pat. No. 10,004,904.

(60) Provisional application No. 61/773,926, filed on Mar. 7, 2013.

(51) Int. Cl.
  *A61N 1/05*   (2006.01)
  *A61N 1/36*   (2006.01)
  *A61N 1/372*  (2006.01)
  *A61N 1/375*  (2006.01)

(52) U.S. Cl.
  CPC ....... *A61N 1/0556* (2013.01); *A61N 1/36125* (2013.01); *A61N 1/3752* (2013.01); *A61N 1/37217* (2013.01)

(58) Field of Classification Search
  CPC .............. A61N 1/36125; A61N 1/3752; A61N 1/37217; A61N 1/0556; A61N 1/375
  See application file for complete search history.

(56) References Cited

U.S. PATENT DOCUMENTS

| | | | |
|---|---|---|---|
| 5,423,873 A | 6/1995 | Neubauer et al. | |
| 5,999,848 A | 12/1999 | Gord et al. | |
| 7,996,089 B2 | 8/2011 | Haugland et al. | |
| 2003/0093130 A1 | 5/2003 | Stypulkowski | |
| 2005/0021104 A1 | 1/2005 | DiLorenzo | |
| 2005/0075680 A1 | 4/2005 | Lowry et al. | |
| 2006/0058588 A1 | 3/2006 | Zdeblick | |
| 2008/0154328 A1 | 6/2008 | Thompson et al. | |
| 2009/0062883 A1 | 3/2009 | Meadows et al. | |
| 2009/0118806 A1 | 5/2009 | Vetter et al. | |
| 2009/0149906 A1 | 6/2009 | Ameri et al. | |

(Continued)

FOREIGN PATENT DOCUMENTS

WO    2008048471 A2    4/2008

OTHER PUBLICATIONS

Extended European Search Report dated Jul. 26, 2016 for European Patent Application No. EP 14760728.

(Continued)

*Primary Examiner* — Michael W Kahelin
(74) *Attorney, Agent, or Firm* — Foley & Lardner LLP

(57) ABSTRACT

A device comprises an implantable pulse generator having a plurality of stimulator outputs and a plurality of neutral electrodes. A lead splitter is configured to electronically map the stimulator outputs to the plurality of neutral electrodes. The present invention generally relates to implanted neurostimulation systems and, more particularly, to a lead splitter for neurostimulation systems and methods to increase the number of effective output channels of a single or multi-channel neurostimulator.

18 Claims, 6 Drawing Sheets

(56) References Cited

U.S. PATENT DOCUMENTS

2011/0022124 A1  1/2011  Zdeblick
2011/0026082 A1  2/2011  Miyadera et al.
2011/0029052 A1  2/2011  McDonald et al.
2012/0071948 A1  3/2012  Pianca et al.
2012/0330384 A1  12/2012  Perryman et al.
2013/0006315 A1  1/2013  Lee

OTHER PUBLICATIONS

Huang, J. et al.: Dilation of the oropharynx via selective stimulation of the hypoglossal nerve:, Journal of Neural Engineering, vol. 2, No. 4, Aug. 2005, pp. 73-80.
Office Action dated Jan. 27, 2016 for Canadian Patent Application No. 2,641,821.
Office action on EP application No. 14760728.7 dated Jan. 4, 2019.
International Search Report and Written Opinion on PCT/US2014/019776 dated May 28, 2014.

LEAD SPLITTER FOR NEUROSTIMULATION SYSTEMS

CROSS-REFERENCE TO RELATED APPLICATIONS

This application is a continuation of U.S. patent application Ser. No. 14/771,625 filed Aug. 31, 2015, which is a U.S. National Stage of International Application No. PCT/US2014/019776, filed Mar. 3, 2014, which claims the benefit of U.S. Provisional Patent Application No. 61/773,926 filed Mar. 7, 2013 entitled "Lead Splitter For Neurostimulation Systems", each of which is incorporated by reference herein in its entirety.

BACKGROUND OF THE INVENTION

The present invention generally relates to implanted neurostimulation systems and, more particularly, to a lead splitter for neurostimulation systems and methods to increase the number of effective output channels of a single or multi-channel neurostimulator.

BRIEF SUMMARY OF THE INVENTION

In one embodiment, there is a neurostimulator (implanted pulse generator or "IPG"), a lead splitter and two leads. The IPG has a single connector port with connections to six output channels and which can be connected to the lead that has six contacts within a cuff electrode. The cuff electrode wraps around a hypoglossal nerve to activate a single hypoglossal nerve and its neural fiber population. The lead splitter has a connector which mates with the IPG so that it receives the six output channel signals of the IPG. The lead splitter has two inline connectors which can be attached to two leads which each have six contacts within cuff electrodes which then wrap around the left and the right hypoglossal nerve. The lead splitter contains an electronic circuit that is housed in a hermetic enclosure. The lead splitter receives power from an internal power source, or an externally applied source or from the IPG output connections. The power source is used to power the circuitry of the lead splitter. The lead splitter receives data from the external power source which is modulated by methods known to those skilled in the art. Alternatively, the lead splitter receives data from the IPG output channels using stimulation pulse frequency, phase duration, and/or waveform shape to impart data information to the lead splitter and to distinguish between stimulation output meant for the lead splitter or for the neural tissues. The lead splitter may be programmed to assign IPG output channels to any of the connected electrode cuff contacts either statically or dynamically during stimulation, and thus effectively increases the number of output channels of the IPG.

In one embodiment there is a device that comprises an implantable pulse generator having a plurality of stimulator outputs; a plurality of neural electrodes; and a lead splitter configured to electronically map the stimulator outputs to the plurality of neural electrodes.

In one embodiment there is a system that comprises: an implantable pulse generator having a plurality of stimulator outputs; a first lead having a first plurality of electrodes each configured to stimulate a portion of a first nerve; a second lead having a second plurality of electrodes each configured to stimulate a portion of a second nerve; and a lead splitter configured to electronically map the plurality of stimulator outputs to the first plurality of electrodes and the second plurality of electrodes. In one embodiment, a total number of stimulator outputs is equal to a total number of the first plurality of electrodes and is equal to a total number of the second plurality of electrodes. In one embodiment, the first plurality of electrodes are coupled to a first cuff configured to at least partially wrap around the first nerve such that the first plurality of electrodes are spaced on the first nerve, and wherein the second plurality of electrodes are coupled to a second cuff configured to at least partially wrap around the second nerve such that the second plurality of electrodes are spaced on the second nerve.

In one embodiment, power is derived from the stimulation pulses of the stimulator outputs. In one embodiment, data is provided to the system using stimulation pulses of the stimulator outputs. In one embodiment, data from the stimulation pulses uses pulse polarity and/or phase to encode data to the system. In one embodiment, data from the stimulation pulses uses multiple pulse phases to encode data to the system. In one embodiment, data from the stimulation pulses uses pulse phase duration to encode data to the system. In one embodiment, data from the stimulation pulses uses pulse frequency to encode data to the system. In one embodiment, the system is able to control whether or not stimulation pulses are passed to the cuff electrode contacts. In one embodiment, the system is able to pass data to secondary systems allowing multiple lead splitters to be attached in sequence to a single port of a neurostimulator.

In one embodiment, the system is able to pass data back to the stimulator. In one embodiment, the method used to communicate back to the stimulator may be controlled by one or more of impedance or load, RF telemetry, optical telemetry, and AC modulation of the wired interface. In one embodiment, the data may contain one or more of electrode contact impedance, system status, system battery condition including state of charge and/or elective replacement indicator information, and system memory storage information and commands to read or write to that storage. In one embodiment, the system is able to disconnect connections to lead contacts for use in protecting tissue from effects of one or more of an MRI, electrocautery, and defibrillation.

In one embodiment, the system contains or connects to sensors that may provide the sensor information to the neurostimulator or its external controller. In one embodiment, the system is configured to pre-process sensor information and transfer that information to the neurostimulator or its external controller. In one embodiment, the system is configured to gain the attention of the neurostimulator through polled or interrupt methods.

BRIEF DESCRIPTION OF THE SEVERAL VIEWS OF THE DRAWINGS

The foregoing summary, as well as the following detailed description of embodiments of the lead splitter for neurostimulation systems, will be better understood when read in conjunction with the appended drawings of an exemplary embodiment. It should be understood, however, that the invention is not limited to the precise arrangements and instrumentalities shown.

In the drawings.

DETAILED DESCRIPTION OF THE INVENTION

Figure 1:
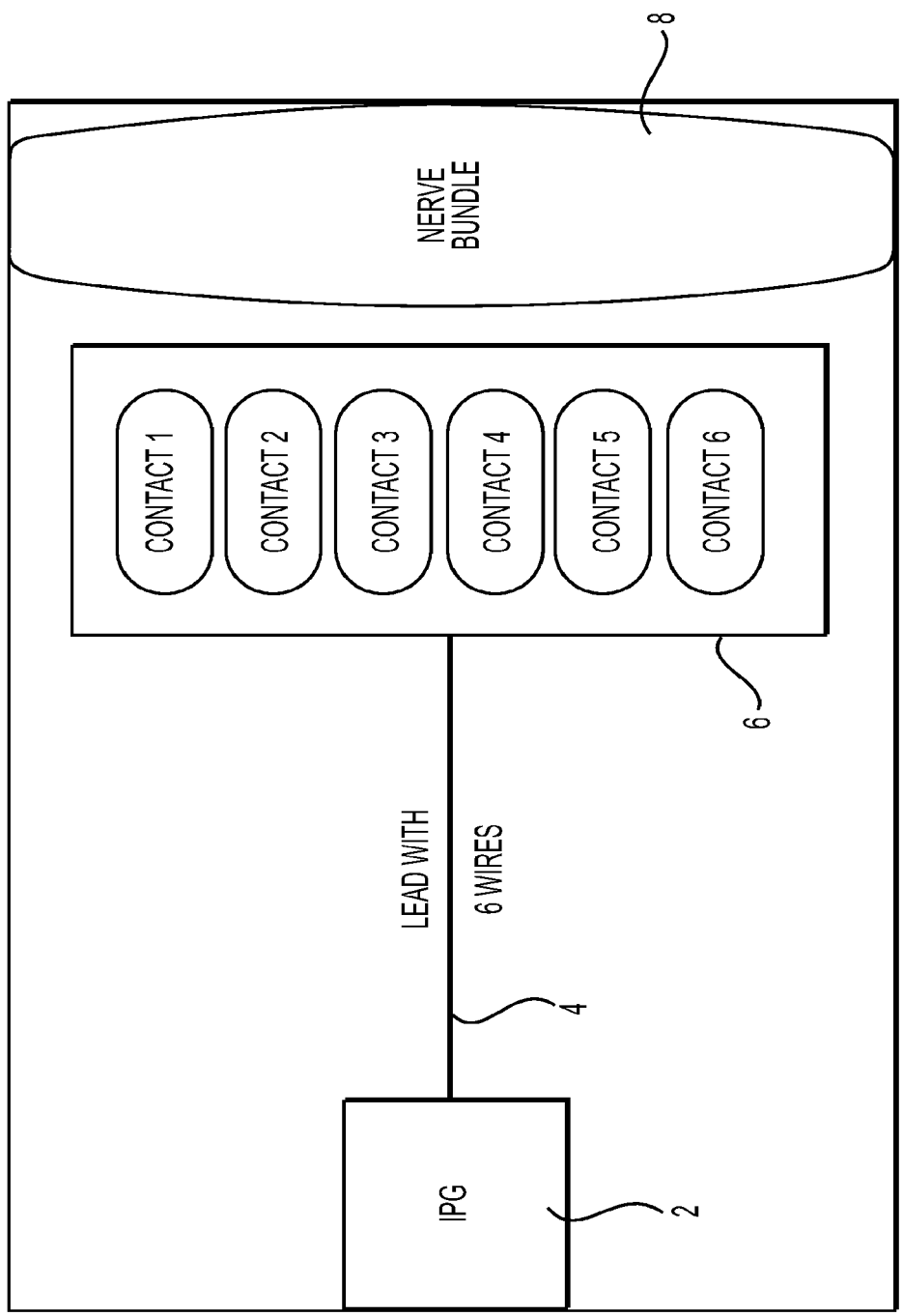
FIG. 1 is a schematic view of a traditional IPG, lead, and cuff electrode.

Implanted neurostimulation systems are designed to have neural interfaces with a fixed number of contacts. A single channel of a neurostimulator may be connected to two metallic or other current passing elements to pass a stimulation waveform between the contacts that is typically in close proximity to the target tissue to be activated. The number of contacts may vary, but in its most elemental and common form, a single channel neurostimulator will have a single contact placed next to a nerve through which current is passed and which is collected by another contact, often the case of the neurostimulator itself.

In many instances, a neurostimulator will have a plurality of contacts such as the systems disclosed in U.S. Patent Application Publication No. 2011/0112601, which is hereby incorporated by reference in its entirety, so that there is a choice as to which portions of a nerve structure may be activated by the electrode attached to the neurostimulator. Such is the case in obstructive sleep apnea ("OSA") in which a single cuff electrode is placed around the proximal hypoglossal nerve to prevent occlusion of the airway during sleep. The ability to effectively utilize this treatment often depends upon the severity of the disease, the most severe of which may not be effectively treated because of a limitation in the number of leads of the neurostimulator—only one hypoglossal nerve can be stimulated. In such situations it may be beneficial to place a second neurostimulation system to also activate the contralateral hypoglossal nerve, but this would entail additional cost, longer surgery, additional external equipment required, and complicate the control and use of a dual implant system.

A solution to this problem is to employ a "lead-splitter", a mechanical interface between the neurostimulator and two or more leads that can be attached. This interface takes the available contacts of the neurostimulator and divides them between the electrodes attached to the splitter. Since the contacts must ordinarily be assigned to a single neurostimulator channel, it could not be expected that a single neurostimulator channel could effectively be connected to two contacts because the neural excitation requirements of those contacts would be different. Therefore, there is a reduction in the number of contacts that can be utilized for each nerve attached to the splitter compared to the single lead.

Referring to the drawings in detail, wherein like reference numerals indicate like elements throughout, there are shown in FIGS. 2-7, a lead splitter, generally designated 10, in accordance with exemplary embodiments of the present invention.

A traditional neurostimulation system, shown in FIG. 1, consists of an implanted neurostimulator or IPG 2, a lead 4, and a cuff electrode 6.

When it is desired to maintain the multi-channel selectivity but increase the number of electrodes supported, the only known solution is to implant an additional neurostimulation system. This is commonly done for deep brain stimulation, spinal cord stimulation and cochlear implants, where bilateral implants in children are quickly becoming the norm. Adding another stimulator to achieve a second neural site of adds significant cost, significant increased surgery time, doubles or at least complicates external patient equipment, and may lead to reduced functionality because of the presence of two devices which likely must use the same telemetry channel for communication to the external system controllers. Additionally, there is the issue of device synchronization which may or may not be possible with the implantation of two completely independent systems.

Figure 2:
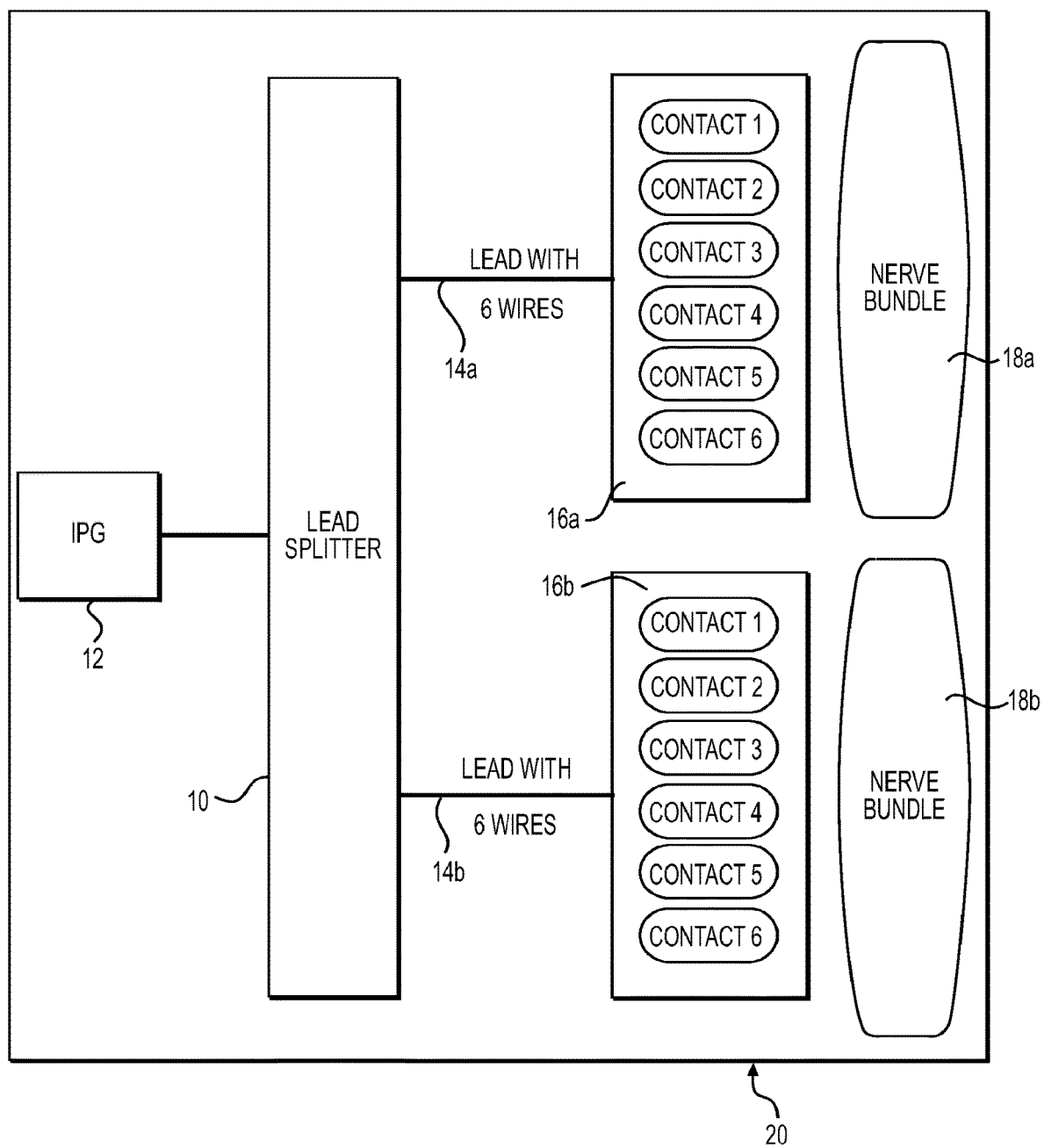
FIG. 2 is a schematic view of a single implanted pulse generator, the lead splitter, and two leads with cuff electrodes in accordance with an exemplary embodiment of the present invention.

The lead splitter 10, as shown in FIG. 2, is an electronic device that allows expansion of a neurostimulation system 20 to support more channels or output connections than the original neurostimulation could support without the lead splitter 10. FIG. 2 depicts a general exemplary arrangement of the invention whereby a single neurostimulator (IPG) 12 is attached to the lead splitter 10 to which is attached two leads 14a, 14b with cuff electrodes 16a, 16b configured to stimulate respective nerves 18a, 18b. In one embodiment, nerves 18a, 18b are hypoglossal nerves. It can be seen that each lead 14a, 14b and cuff electrode 16a, 16b have the same number of contacts available to the nerve bundle 18a, 18b as in the single lead and cuff electrode configuration (see FIG. 1).

In one embodiment, the pulse generator has one or more stimulator outputs, one or more neural electrodes, and a lead splitter configured to electronically map the one or more stimulator outputs to the one more neural electrodes. In one embodiment there is a system that comprises an implantable pulse generator having a plurality of stimulator outputs, a first lead having a first plurality of electrodes each configured to stimulate a portion of a first nerve, a second lead having a second plurality of electrodes each configured to stimulate a portion of a second nerve, and a lead splitter configured to electronically map the plurality of stimulator outputs to the first plurality of electrodes and the second plurality of electrodes. In one embodiment, a total number of stimulator outputs is equal to a total number of the first plurality of electrodes and is equal to a total number of the second plurality of electrodes. In one embodiment, the total number of the first plurality of electrodes is unequal to the total number of the second plurality of electrodes. In one embodiment, the total number of the first plurality of electrodes is unequal to the total the number of stimulator outputs.

Figure 3:
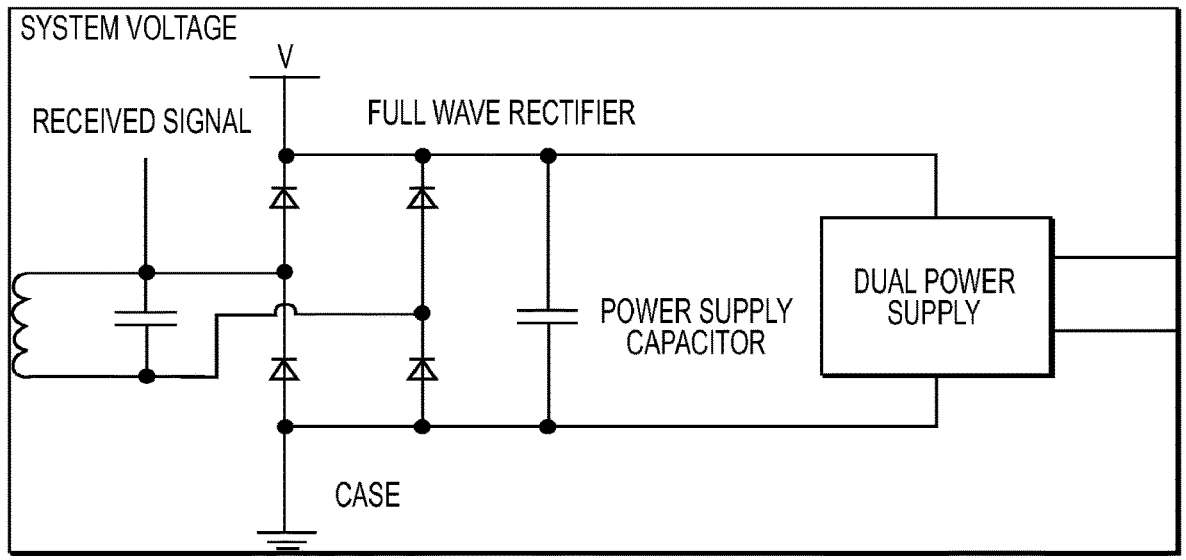
FIG. 3 is a schematic view of the induction power and data signal reception portion of the lead splitter shown in FIG. 2.

In one embodiment, the lead splitter has a simple power source. This could be battery powered as is the IPG, but other methods of powering the device are possible as well. FIG. 3 depicts a method of induction power whereby the lead splitter receives power and data from an external source and stores this power for use by the lead splitter in a power storage element, such as a capacitor. Because in some instances the lead splitter will receive data rarely, such as on initial power up and use, the operating current of maintaining switch conditions may allow the lead splitter to operate off only the stored power received by the capacitor and it may not need to have an internal battery.

Figure 4:
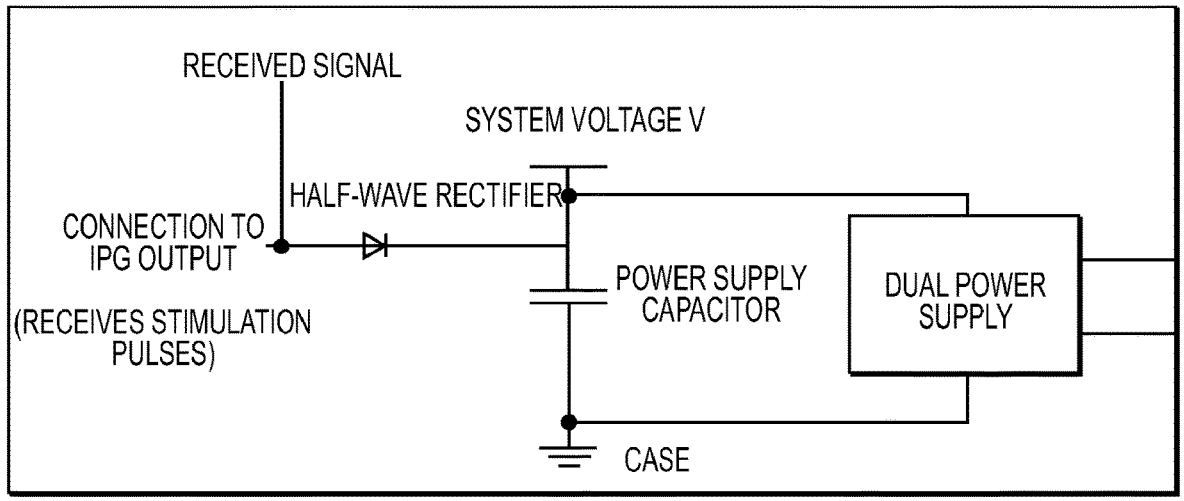
FIG. 4 is a schematic view of the stimulation alternative employing pulse power and data signal reception portion of the lead splitter shown in FIG. 2.

FIG. 4 depicts another method of power and data transfer to the lead splitter in which power and data are derived from the stimulation pulses supplied by the IPG. This may simplify the use of the device as power and control are derived from the IPG rather than from additional external devices or methods. In both methods depicted in FIGS. 3 and 4 power is converted to a format required for the faithful switching and passage from the stimulator outputs to the leads and connectors such that the stimulation waveforms are affected adversely as little as possible. This is also important for charge balance so that charge neutrality is maintained in the stimulated nerve.

Figure 5:
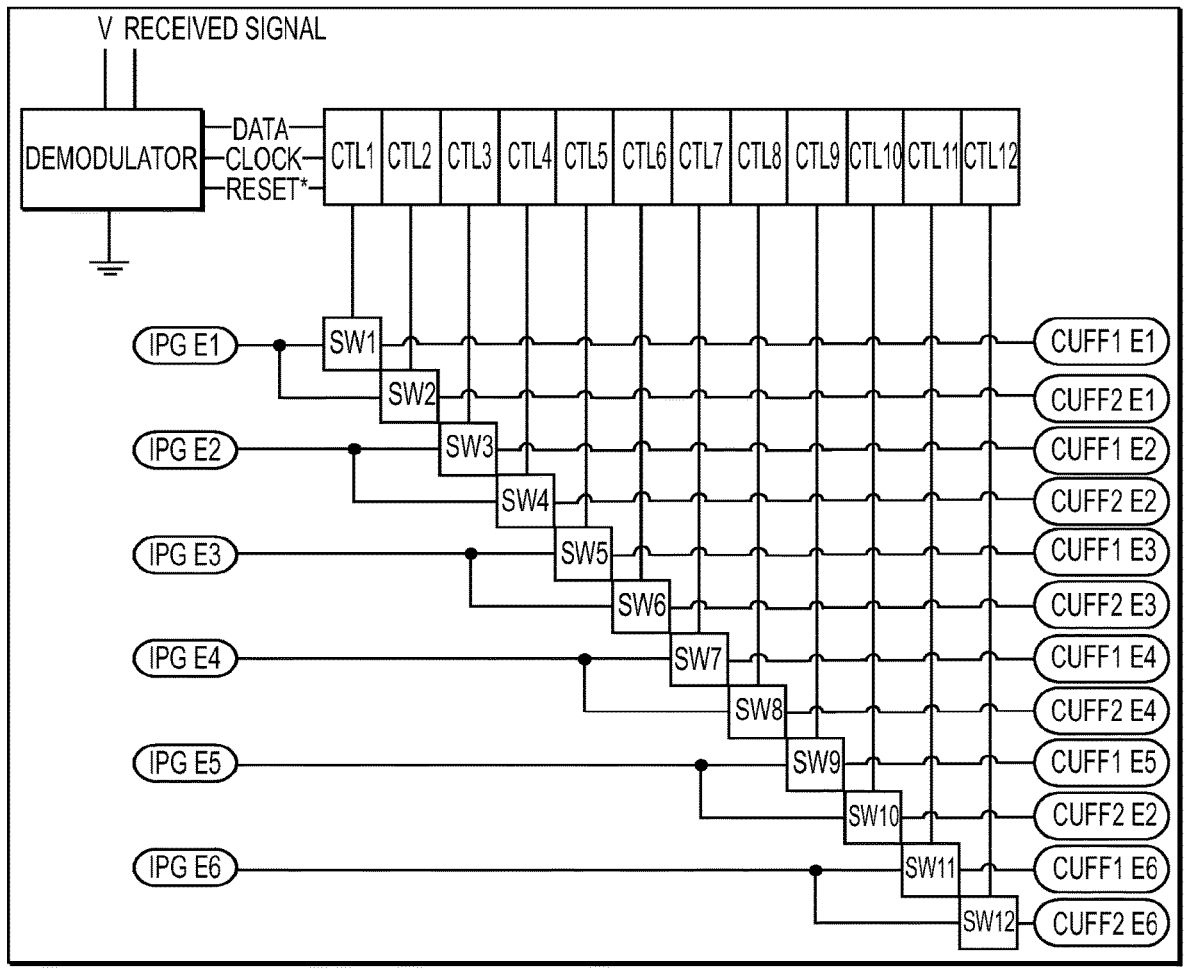
FIG. 5 is a schematic view of the data demodulator, shift register, analog switches, input connections to the IPG stimulation outputs and output connections to two leads and cuff electrodes shown in FIG. 2.

FIG. 5 depicts a configuration of the lead splitter having a data demodulator to receive and decode the incoming data, a shift register controlled by the demodulator, whose outputs control a bank of analog switches which direct the stimulator outputs either to contacts on one of two connected leads and electrodes.

Figure 6:
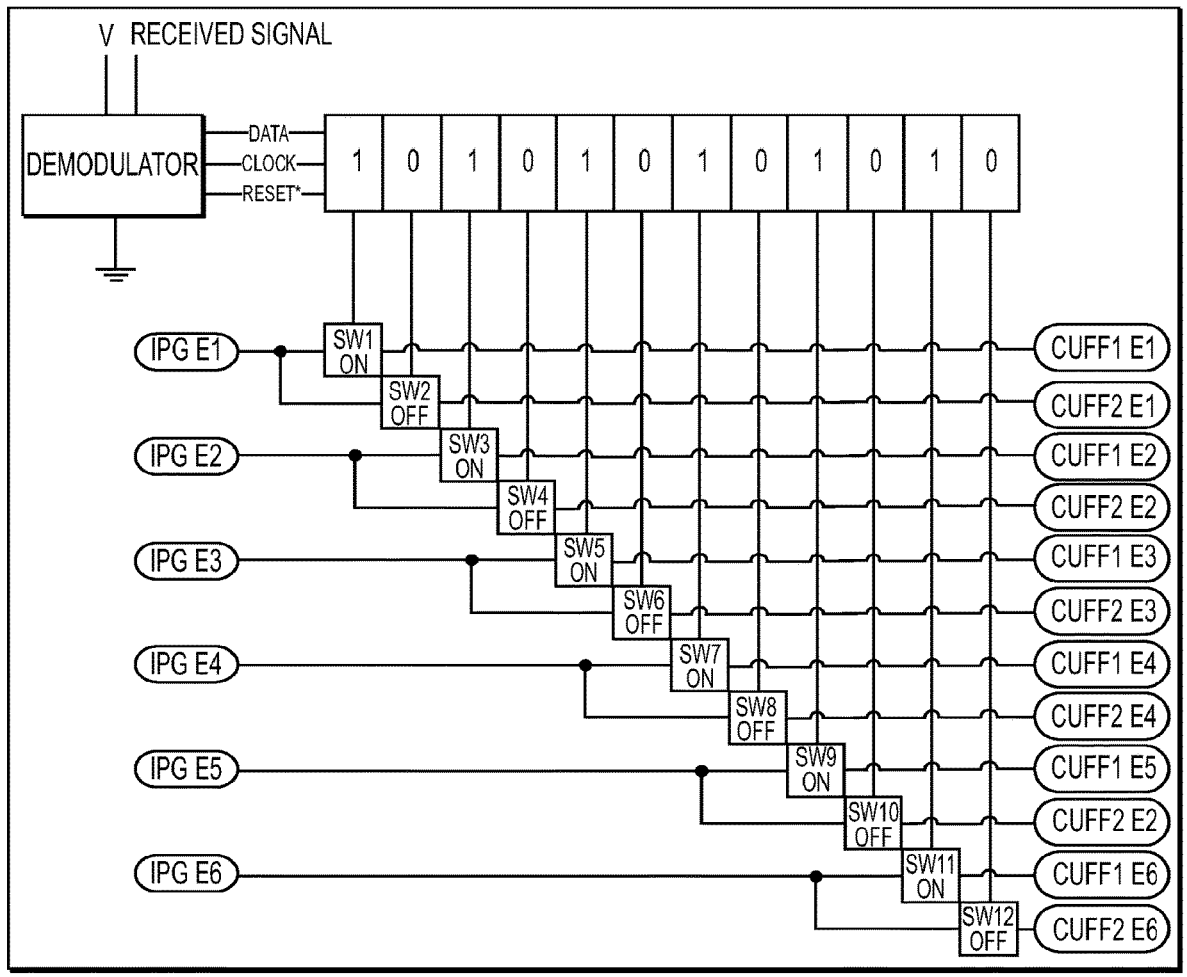
FIG. 6 is a schematic view of the default condition of the lead splitter of FIG. 5 showing three contacts of each cuff electrode assigned to three outputs of the IPG.

FIG. 6 depicts a configuration of the lead splitter in its default condition in which the first three outputs of the IPG are connected to the first three contacts of one cuff electrode and the second three outputs of the IPG are connected to the last three contacts of the second cuff electrode. This is just an example, the contacts may be assigned to either of the cuff electrodes in any order up to the number of outputs available from the IPG.

Figure 7:
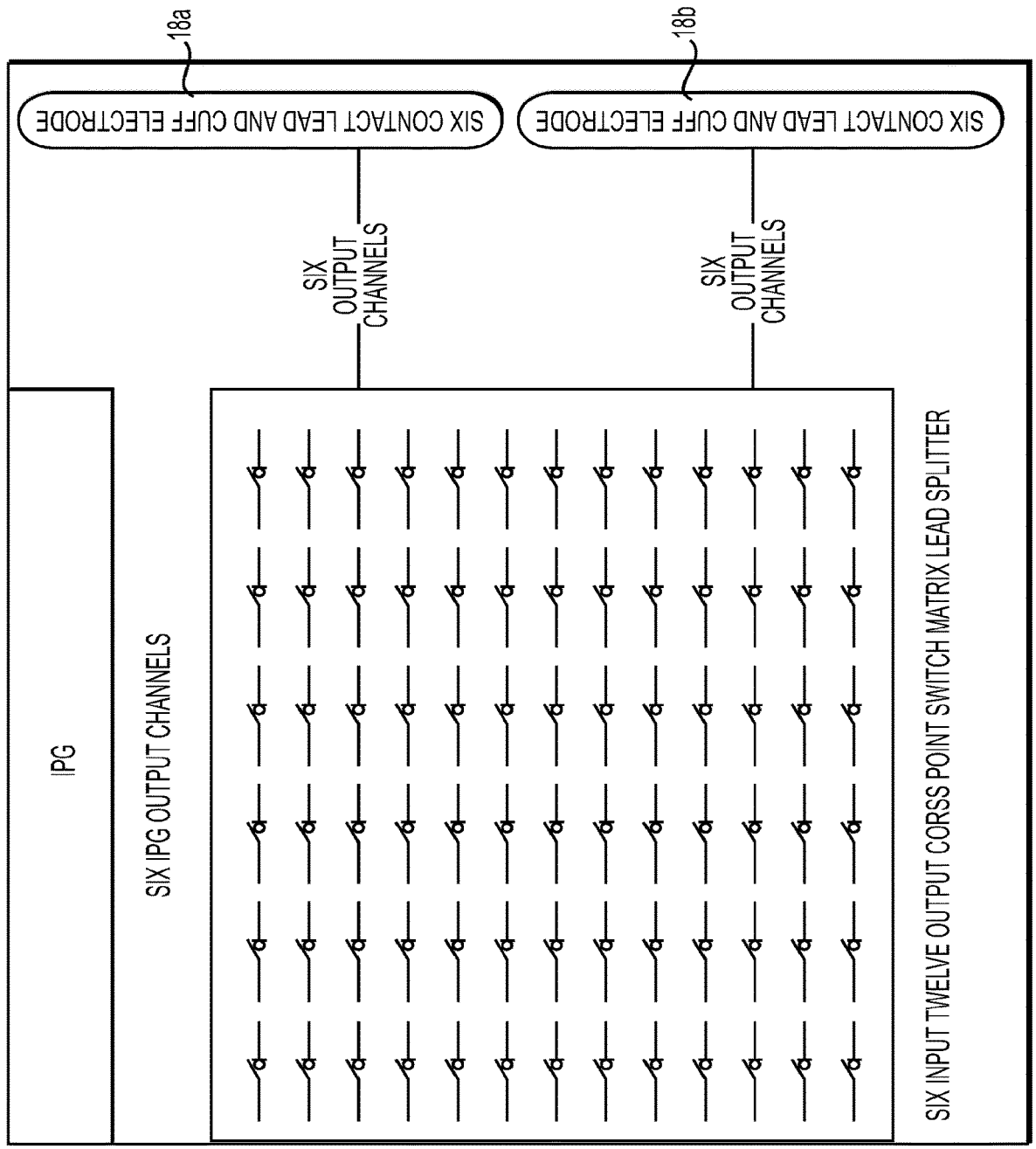
FIG. 7 is a schematic view of a full cross-point switch matrix embodiment of the lead splitter shown in FIG. 2 allowing assignment of any IPG output channel to any of the twelve cuff electrode contacts.

FIG. 7 depicts a configuration of the lead splitter in which a full cross-point switch matrix is utilized to map any IPG output to any of the potential 12 contacts in this two lead and cuff electrode example. This allows the use of a contact that might be lost due to a broken lead wire that might otherwise reduce the available output channels in a traditional connection method.

Utilizing the electronic lead splitter described herein, the total number of outputs of the IPG may be utilized on all split outputs—6 IPG outputs may be utilized on one split lead and 6 may be utilized on the other—or any sub-set in between may be utilized.

The contact assignments would normally be configured once at the start of a stimulation treatment therapy session but could be re-configured as often as necessary. This, for instance, could allow assignment of contacts first to one cuff electrode, then alternately be assigned at a later time to another. This would essentially allow all contacts to be available and active on both cuff electrodes as if there were actually were two independent systems implanted.

Data input to the induced power system can be achieved by any method known to those skilled in the art. Device identification and data integrity checks would likely be required because of the wireless link to the device, but could be easily accommodated by any of several known methods.

Data input to the lead splitter by the pulse input method could be achieved by using stimulation pulses that would not normally be used during stimulation. For instance, typical stimulation parameters would normally have cathodic phase durations in excess of 200 µs. Pulses that were shorter than 200 µs could be used to disconnect the pulses from the cuff electrodes and then could be used to impart data messages to the lead splitter. Pulse spacing, width, or special shape pulses could also be used for this purpose.

Pulses could employ shape to indicate data rather than stimulation. Normal stimulation would likely present the cathodic phase first, followed by the charge recovery anodic phase. Changing this to present the anodic phase first could signal the lead splitter that these pulses contain data to the lead splitter. Advantageously, this would allow high amplitude anodic phase amplitudes followed by long phase duration but low amplitude cathodic phases should it be desired to allow these stimulation pulses to pass to the tissue as they would not be likely to cause neural excitation. The use of this reversed waveform would allow pulses of any frequency normally applied by the stimulation system to be employed in once manner for stimulation and in the other for power and data for the lead splitter.

Another method to apply power to the lead splitter would be the use of higher frequency pulses. In the OSA application, pulse frequencies range from 1 to 100 pps. Frequencies above this could indicate to the lead splitter that the pulses contain power and data and they could be prevented from passage to the cuff electrodes.

The pulse method of power and data transfer from the IPG to the lead splitter may reduce the need for identification qualification of the incoming data to the lead splitter from the IPG—the origin of the data is determined by hard wired connections. This also ensures data integrity since wireless telemetry methods would not be employed—hardwired communication methods may be more robust than wireless methods.

The use of high frequency stimulation to impart data and power could employ normal polarity and reversed polarity pulses to signify data. Cathodic phase first could signify a data '1' and anodic phase first could signify a data '0'.

In one embodiment, the data received from the neurostimulator is pulse phase. In one embodiment, the data received is pulse phase duration, either longer or shorter than treatment pulse duration. In one embodiment, the data received may be pulse frequency. In one embodiment, data received is phase order—cathodic first is "1", anodic first is "0", etc. In one embodiment, data received is multi-phasic—special sync pulses or other special pulses could employ three or more phases.

Using very narrow cathodic and anodic phase but symmetrical biphasic waveforms would ensure that even if the first pulse were to be passed to the neural tissue that it would likely be below excitation threshold.

It may be desirable to use a lead splitter on each lead of a multi-lead neurostimulation system. Control of each lead splitter would be identical to the single lead system for each lead. It may be desirable to use multiple lead splitter devices to increase the output contact capability to greater than what could be achieved in a single lead splitter device. The lead splitter decoder circuitry could be instructed to pass data on to the next lead splitter device without decoding the data for its own use. This would allow downstream devices to be controlled by the single lead connection of the neurostimulator.

It may be desirable to feed data back to the neurostimulator. Normally, neurostimulator outputs are used to generate output pulses, not receive data. But, many neurostimulators are able to measure the impedance of the lead connections to the lead contacts. This is useful to monitor the performance of the neural interface over time as well as to detect the failure of a wire or connection in a lead. The neurostimulator would be able to measure the impedance of the neurostimulator to tissue impedance as normal, but the lead splitter could employ a controlled impedance that could be used on command to interrogate the lead splitter on the state of the lead splitter or to conduct other functions such as independent impedance measurement functions, state of power source, etc.

Another method to feed data back to the neurostimulator would be to modulate the stimulator output connections coming into the lead splitter. A neurostimulator could be designed with this function in mind to allow this reverse data pathway.

In one embodiment, the lead splitter provides feedback to the neurostimulator via special function controlled impedance load to the neurostimulator. In one embodiment, the special function is lead splitter contact impedance. In one embodiment, the special function is state of charge of the lead splitter power source. In one embodiment, the special function is the serial number of the lead splitter. In one embodiment, the special function is the programming and reading of memory in the lead splitter. In one embodiment, the special function is the transfer of connection from the neurostimulator to a complex load for other functions (MRI compatibility, etc.). In one embodiment, the lead splitter uses control of special impedance load to feed information back to the neurostimulator. In one embodiment, the lead splitter modulates the connection to the IPG with pulsatile information that a neurostimulator designed to receive such information may use to receive return data. In one embodiment, the lead splitter incorporates or connects to a sensor and may transmit this sensor information back to the neurostimulator. In one embodiment, the lead splitter incorporates other communications such as RF that may transmit information back to the neurostimulator. In one embodiment, the lead splitter incorporates optical methods to transmit information back to the neurostimulator. On one embodiment, the lead splitter incorporates modulation circuitry to provide an AC waveform to the stimulation output leads that may be sensed and decoded by the neurostimulator.

It certain embodiments, it may be desirable to change the properties of the implanted neurostimulator for special situations. Magnetic Resonance Imaging (MRI) is routinely used for patients without implanted neurostimulation systems. The lead splitter could, under special function control, change the connections to the neurostimulator to facilitate exposure to MRI and prevent damage to the patient.

It may be desirable to incorporate a sensor or sensors in a lead splitter to provide additional data to a neurostimulator. Sensors could be used for measurement of oxygen concentration, position, etc.

It may be desirable to provide surge protection or other Electromagnetic Interference (EMI) or Electromagnetic Compatibility (EMC) protection to the lead splitter, which could be controlled by the neurostimulator or independently of the neurostimulator both to protect the lead splitter and to protect the neurostimulator. The lead splitter may incorporate surge or EMC or EMI protection circuitry, automatically or under control of the neurostimulator or an external controller.

In one embodiment, there is one lead splitter per lead. In one embodiment, there is more than one lead splitter per lead (e.g., data structure allows daisy-chaining multiple lead splitters on a single lead).

In one embodiment, a system incorporating a lead splitter described herein may include one or more computers having one or more processors and memory (e.g., one or more nonvolatile storage devices). In some embodiments, memory or computer readable storage medium of memory stores programs, modules and data structures, or a subset thereof for a processor to control and run the various systems and methods disclosed herein. In one embodiment, a non-transitory computer readable storage medium having stored thereon computer-executable instructions which, when executed by a processor, perform one or more of the methods disclosed herein. In some embodiments the lead splitter is able to inform the neurostimulator of certain conditions, either by the neurostimulator requesting information of the lead splitter, or the lead splitter sending a trigger to the neurostimulator such that information interchange may occur.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

I claim:

1. A system comprising:
    an implantable pulse generator having a plurality of stimulator outputs each providing a plurality of stimulator pulses;
    a first lead having a first plurality of electrodes each configured to stimulate a portion of a first nerve;
    a second lead having a second plurality of electrodes each configured to stimulate a portion of a second nerve; and
    a lead splitter electrically coupled between the implantable pulse generator and the first plurality and second plurality of electrodes and configured to selectively assign the plurality of stimulator outputs to the first plurality of electrodes and the second plurality of electrodes to deliver the plurality of stimulator pulses from the implantable pulse generator to the first plurality of electrodes and the second plurality of electrodes,
    wherein the lead splitter is an electronic lead splitter programmable to permit reconfigurable assignment of the plurality of stimulator outputs to the first plurality of electrodes and the second plurality of electrodes.

2. The system of claim 1, wherein a total number of the plurality of stimulator outputs is equal to a total number of the first plurality of electrodes and is equal to a total number of the second plurality of electrodes.

3. The system of claim 1, wherein the first plurality of electrodes are coupled to a first cuff configured to at least partially wrap around the first nerve such that the first plurality of electrodes are spaced on the first nerve, and wherein the second plurality of electrodes are coupled to a second cuff configured to at least partially wrap around the second nerve such that the second plurality of electrodes are spaced on the second nerve.

4. The system of claim 1, wherein the lead splitter requires power to selectively assign each of the plurality of stimulator outputs, the power being derived from the plurality of stimulation pulses.

5. The system of claim 4, wherein the lead splitter requires data to selectively assign each of the plurality of stimulator outputs, the data being provided to the lead splitter using the plurality of stimulation pulses.

6. The system of claim 5, wherein the implantable pulse generator uses pulse polarity and/or phase of the plurality of stimulation pulses to encode the data.

7. The system of claim 5, wherein the implantable pulse generator uses multiple pulse phases to encode the data.

8. The system of claim 5, wherein the implantable pulse generator uses pulse phase duration to encode the data.

9. The system of claim 5, wherein the implantable pulse generator uses pulse frequency to encode the data.

10. The system of claim 4, wherein the lead splitter is configured to control whether or not the plurality of stimulation pulses are passed to the first plurality of electrodes and/or the second plurality of electrodes.

11. The system of claim 4, wherein the lead splitter is able to pass data to a secondary lead splitter allowing multiple lead splitters to be attached in sequence to a single port of the implantable pulse generator.

12. The system of claim 1, wherein the lead splitter is configured to pass data back to the implantable pulse generator.

13. The system of claim 12, wherein the lead splitter is configured to communicate back to the implantable pulse generator by one or more of impedance or load, RF telemetry, optical telemetry, and AC modulation.

14. The system of claim 12, wherein the data contains one or more of electrode contact impedance, status of the lead splitter, power condition of the lead splitter including state of charge and/or elective replacement indicator information, and memory storage information retrieved by the implantable pulse generator using commands from the implantable pulse generator to the lead splitter to read from or write to memory storage of the lead splitter.

15. The system of claim 1, wherein the lead splitter is configured to disconnect connections to the first plurality of electrodes and/or the second plurality of electrodes to protect tissue from effects of one or more of an MRI, electrocautery, and defibrillation or other potentially harmful electromagnetic conditions or environments.

16. The system of claim 1, wherein the lead splitter contains or connects to one or more sensors configured to provide information to the lead splitter or an external controller.

17. The system of claim 16, wherein the lead splitter is configured to pre-process the information and transfer that information to the implantable pulse generator or the external controller.

18. The system of claim 16, wherein the lead splitter and the implantable pulse generator are configured to communicate with one another through polled or interrupt methods.

\* \* \* \* \*